(12) United States Patent
Ostermeyer et al.

(10) Patent No.: US 10,018,520 B2
(45) Date of Patent: Jul. 10, 2018

(54) TEMPERATURE CALIBRATION FOR A MEASURING APPARATUS

(71) Applicant: Anton Paar OptoTec GmbH, Seelze-Letter (DE)

(72) Inventors: Martin Ostermeyer, Gehrden (DE); Thomas Brandl, Hannover (DE)

(73) Assignee: Anton Paar OptoTec GmbH, Seelze-Letter (DE)

( * ) Notice: Subject to any disclaimer, the term of this patent is extended or adjusted under 35 U.S.C. 154(b) by 100 days.

(21) Appl. No.: 15/140,201

(22) Filed: Apr. 27, 2016

(65) Prior Publication Data
US 2016/0320252 A1    Nov. 3, 2016

(30) Foreign Application Priority Data

Apr. 30, 2015   (DE) ........................ 10 2015 106 805

(51) Int. Cl.
| | |
|---|---|
| *G01K 15/00* | (2006.01) |
| *G01N 21/41* | (2006.01) |
| *G01N 21/27* | (2006.01) |
| *G01N 21/43* | (2006.01) |
| *G01N 21/552* | (2014.01) |
| *G01N 21/35* | (2014.01) |

(52) U.S. Cl.
CPC ......... *G01K 15/005* (2013.01); *G01N 21/274* (2013.01); *G01N 21/4133* (2013.01); *G01N 21/43* (2013.01); *G01N 21/552* (2013.01); *G01N 2021/3595* (2013.01); *G01N 2021/414* (2013.01); *G01N 2201/1211* (2013.01)

(58) Field of Classification Search
None
See application file for complete search history.

(56) References Cited

U.S. PATENT DOCUMENTS

| | | | |
|---|---|---|---|
| 5,362,445 A | 11/1994 | Miyahara et al. | |
| 6,517,240 B1 * | 2/2003 | Herb ...................... | G01K 11/24 |
| | | | 374/117 |

(Continued)

FOREIGN PATENT DOCUMENTS

| | | |
|---|---|---|
| DE | 42 25 996 A1 | 2/1993 |
| DE | 203 18 964 U1 | 4/2004 |

(Continued)

*Primary Examiner* — Lisa Caputo
*Assistant Examiner* — Nasir U Ahmed
(74) *Attorney, Agent, or Firm* — Robert A. Blaha; Smith Tempel Blaha LLC (57) ABSTRACT

Measuring apparatus-calibration device for calibrating a measuring apparatus-temperature sensor of a, in particular optical, measuring apparatus, wherein the measuring apparatus-calibration device comprises a, preferably measuring apparatus-external, calibration-temperature sensor, which is traceably calibratable itself, for determining a calibration temperature in the region of a measuring surface of the measuring apparatus and a determination unit which is adapted for determining an information which is indicative for a discrepancy between a measuring apparatus-temperature which is captured by the measuring apparatus-temperature sensor in the region of the measuring surface and the calibration temperature, on whose basis the measuring apparatus-temperature sensor is calibratable.

19 Claims, 4 Drawing Sheets

(56) References Cited

U.S. PATENT DOCUMENTS

| | | | |
|---|---|---|---|
| 6,596,973 B1 | 7/2003 | Donald et al. | |
| 7,064,816 B2 | 6/2006 | Langenbacher et al. | |
| 8,177,421 B2 | 5/2012 | Liebmann | |
| 8,231,266 B2* | 7/2012 | Schulze | G01K 15/00 374/1 |
| 8,239,144 B2* | 8/2012 | Fedele | G01N 21/4133 356/128 |
| 8,280,674 B2 | 10/2012 | Schwerer et al. | |
| 2006/0171442 A1* | 8/2006 | Volf | G01J 5/0003 374/1 |
| 2010/0020330 A1* | 1/2010 | Owen | G03F 7/70508 356/499 |
| 2010/0286842 A1* | 11/2010 | Aggarwal | G01K 1/02 700/300 |
| 2013/0223472 A1* | 8/2013 | Maston | G01K 15/00 374/2 |

FOREIGN PATENT DOCUMENTS

| | | |
|---|---|---|
| EP | 0 583 007 A1 | 2/1994 |
| EP | 1 462 782 A1 | 9/2004 |
| GB | 2266271 A | 10/1993 |
| GB | 2266771 A | 10/1993 |
| WO | WO2007020140 A1 | 2/2007 |

\* cited by examiner

TEMPERATURE CALIBRATION FOR A MEASURING APPARATUS

CROSS-REFERENCE TO RELATED APPLICATIONS

This application claims the benefit of the filing date of German Patent Application No. 10 2015 106 805.2 filed 30 Apr. 2015, the disclosure of which is hereby incorporated herein by reference.

TECHNICAL FIELD

Embodiments of the invention relate to a measuring apparatus-calibration device, a measuring apparatus, an arrangement, a method for calibrating a measuring apparatus-temperature sensor of a measuring apparatus and a use.

TECHNICAL BACKGROUND

With a refractometer, a refractive index of a substance can be measured. The refractive index of a substance or a sample depends from both the wavelength of the light and from its temperature. In order to make measuring results comparable, in refractometers, it is therefore often measured at specified wavelengths and temperatures. Deviations from standardized wavelengths or temperatures during measuring lead to measuring errors in many cases. In addition, there are measuring errors of the sensor technology which are specific for the respectively related measuring principle.

In refractometers and in other, in particular optical, measuring apparatuses inaccuracies may occur, if a temperature sensor for measuring the temperature of a sample carrier which is carrying the sample changes its properties over time.

Prior art is disclosed in EP 0,583,007, U.S. Pat. No. 7,064,816, U.S. Pat. No. 6,596,973, U.S. Pat. No. 8,280,674, U.S. Pat. No. 8,177,421, GB 2,266,271 and EP 2,100,112.

SUMMARY

There may be a need for enabling a precise operation of an, in particular optical, measuring apparatus.

The subject-matters with the features according to the independent claims are provided. Further embodiments are shown in the dependent claims.

According to an embodiment of the present invention, a measuring apparatus-calibration device for calibrating a measuring apparatus-temperature sensor of an, in particular optical, measuring apparatus is provided, wherein the measuring apparatus-calibration device comprises a, preferably measuring apparatus-external, calibration-temperature sensor, which itself is traceably calibratable, for determining a calibration-temperature in the region of a measuring surface of the measuring apparatus (i.e. a temperature value for the region of the measuring surface as it is yielded from a measuring by the calibration-temperature sensor) and comprises a determination unit (for example a processor or a part thereof) which is adapted for determining an information (in particular a, further in particular quantitative, information with regard to the detuning or decalibration of a temperature measuring by the measuring apparatus-temperature sensor with respect to an error-free temperature measurement) which information is indicative for a discrepancy between (a) a measuring apparatus-temperature in the region of the measuring surface (i.e. a temperature value for the region of the measuring surface as it is yielded in a measuring by the measuring apparatus-temperature sensor), which measuring apparatus-temperature is captured by the measuring apparatus-temperature sensor, and (b) the calibration-temperature, on whose basis (on the basis of the information) the measuring apparatus-temperature sensor is calibratable or is calibrated.

According to a further embodiment of the present invention, a measuring apparatus is provided, in particular an optical measuring apparatus (i.e. a measuring apparatus which, for measuring a sample, uses electromagnetic radiation, in particular of the visible wavelength range and/or the infrared wavelength range and/or the ultraviolet wavelength range) for, in particular optical, measuring of a sample to be arranged at a measuring surface, wherein the measuring apparatus comprises a measuring apparatus-temperature sensor for capturing a measuring apparatus-temperature in the region of the measuring surface, and comprises an adjusting unit (for example a processor or a part thereof) which is adapted for cooperating with a, preferably at least partially measuring apparatus-external, measuring apparatus-calibration device with the above described features, such that by means of the adjusting unit based on the information which is determined by means of the determination unit of the measuring apparatus-calibration device, the measuring apparatus-temperature sensor is adjustable.

According to a further embodiment of the present invention, an arrangement is provided which comprises an, in particular optical, measuring apparatus, in particular with the above described features, for, in particular optical, measuring of a sample to be arranged at a measuring surface and with a measuring apparatus-temperature sensor for capturing a measuring apparatus-temperature in the region of a measuring surface, and comprises a measuring apparatus-calibration device, in particular with the above described features, with a, preferably measuring apparatus-external, calibration-temperature sensor, which itself is traceably calibratable, for determining a calibration-temperature in the region of the measuring surface of the measuring apparatus for calibrating (and adjusting, respectively) the measuring apparatus-temperature sensor.

According to another embodiment of the present invention, a method for calibrating a measuring apparatus-temperature sensor of an, in particular optical, measuring apparatus is provided, wherein in the method (i) a calibration-temperature in the region of a measuring surface of the measuring apparatus is determined by a, preferably measuring apparatus-external, calibration-temperature sensor, which itself is traceably calibratable and (ii) an information is determined which is indicative for a discrepancy between (a) a measuring apparatus-temperature in the region of the measuring surface, which measuring apparatus-temperature has been captured by a measuring apparatus-temperature sensor and (b) the calibration-temperature, on whose basis (on the basis of the determined information) the measuring apparatus-temperature sensor is calibratable or calibrated.

According to yet another exemplary embodiment of the invention, a measuring apparatus-calibration device with the above described features is used for calibrating a measuring apparatus-temperature sensor which is firmly mounted in a measuring apparatus, in particular with the above described features, or is in a state mounted in the measuring apparatus at least when calibrating (wherein the measuring apparatus may be in particular used for measuring a target quantity (for example a property of the sample, further in particular a refractive index of the sample, an absorption behavior of the sample etc.) which is different from the temperature captured by the measuring apparatus-temperature sensor).

In the context of the present application, the term "in the region of the measuring surface" in particular denotes that the temperature measuring (in particular spatially and/or thermally) is carried out as near as possible to a position of an in particular optically transparent sample carrier at which the sample is arranged in the measuring operation, namely at the measuring surface and on the measuring surface, respectively. In the optical measuring operation, electromagnetic radiation can propagate through the sample carrier. The measuring apparatus-temperature sensor should be spatially arranged as near as possible to and in thermal contact with the measuring surface, but at the same time such that it does not disturb the electromagnetic radiation in the measuring operation. Preferably this is achieved by integrating the measuring apparatus-temperature sensor in the sample carrier. Likewise, the calibration-temperature sensor should be spatially arranged as near as possible to and in thermal contact with the measuring surface, but at the same time also such that it does not disturb the electromagnetic radiation in the measuring operation and such that it is detachable from the measuring apparatus for its own re-calibration. Preferably, this is achieved by attaching the measuring apparatus-temperature sensor onto the sample carrier for calibrating or otherwise coupling it with the sample carrier for capturing its thermal properties and removing the measuring apparatus-temperature sensor during the measuring operation, so that the sample to be measured can be arranged on the sample carrier.

In the context of the present application, the term "traceably calibratable sensor" in particular denotes a sensor which itself is accessible for its own re-calibration by a norm-calibrator. In other words, such a sensor allows for being calibrated itself, for example when it has lost its temperature capturing accuracy. Thereby, it can be ensured that errors due to an inaccurate or lost (for example over time) self-calibration of the sensor can be suppressed and balanced out again, respectively.

An "at least partially measuring apparatus-external sensor" in particular denotes such a one which, in operation or even always, comprises at least one sub-region which is spatially arranged outside of the measuring apparatus. A respective, at least partially measuring apparatus-external measuring apparatus-calibration device is calibratable especially good and easily traceably calibratable, respectively, since it can be detached from the measuring apparatus in order to calibrate the calibration-temperature sensor (and optionally also an optional additional reference-temperature sensor) by a norm-calibrator.

In the context of the present application, the term "information indicative for a discrepancy" denotes in particular the qualitative information, that (i) the measuring apparatus-temperature in the region of the measuring surface, which is captured by the measuring apparatus-temperature sensor on the one hand, and (ii) the calibration-temperature in the region of the measuring surface, which is captured by the calibration-temperature sensor on the other hand, deviate from each other, or denotes the quantitative information to which extent (i) the measuring apparatus-temperature in the region of the measuring surface, which is captured by the measuring apparatus-temperature sensor, and (ii) the calibration-temperature in the region of the measuring surface, which is captured by the calibration-temperature sensor, deviate from each other.

According to an embodiment of the present invention, a temperature calibrating of a measuring apparatus-temperature sensor is provided which is integrated in a measuring apparatus, in particular in an optically transparent sample carrier of an optical measuring apparatus, which complies with the highest accuracy requirements. For this purpose, according to an exemplary embodiment, a calibration-temperature sensor is used which is traceably calibratable itself, therefore not firmly and non-separatably, respectively, integrated in the measuring apparatus. Since it can be calibrated itself, if necessary, before calibrating the measuring apparatus-temperature sensor, it can be reliably trusted upon the high accuracy of a temperature measuring by means of the calibration-temperature sensor in the context of calibrating, which positively effects the precision of the calibrating and finally the precision of the temperature measuring of the calibrated measuring apparatus-temperature sensor. Descriptively, according to an exemplary embodiment of the invention, a measuring apparatus-temperature sensor which is firmly mounted in a measuring apparatus, for capturing a temperature at an application location of the sample, is calibratable by means of a calibration-temperature sensor which is provided separated from the measuring apparatus or is at least separable from the measuring apparatus, which calibration-temperature sensor itself is accessible to a calibration by a normed calibration scale.

In the following, additional exemplary embodiments of the measuring apparatus-calibration device, the measuring apparatus, the arrangement, the method and the use are described.

According to an exemplary embodiment, the calibration-temperature sensor may be a surface temperature sensor for measuring apparatus-external, coupling to (in particular for attaching onto) the measuring surface. According to this especially preferred embodiment, for a temperature measurement which is carried out for calibrating, the calibration-temperature sensor of the measuring apparatus-calibration device can be attached easily from outside as a calibration probe onto the measuring surface on which in the measuring operation the sample to be measured is attached for an interaction with the electromagnetic radiation of the optical measuring apparatus. By this non-invasive process, the optical sensor path in an interior of the measuring apparatus remains undisturbed by the calibration and is not threatened to be misadjusted.

According to an alternative exemplary embodiment, the calibration-temperature sensor may be fixed in an interior of the measuring apparatus at and/or in a sample carrier which comprises the measuring surface. Advantageously, the calibration-temperature sensor according to this embodiment should also be detachable from the measuring apparatus for being delivered itself to a self-adjusting and/or a self-calibrating, if necessary. This embodiment leads to an especially compact arrangement and enables a very accurate calibration measuring very close to the measuring apparatus-temperature sensor.

According to an exemplary embodiment, the calibration-temperature sensor can be a thermometer (for example a resistance thermometer which is attached onto the measuring surface with a physical contact) which is contact-afflictedly attachable onto the measuring surface. Alternatively, the calibration-temperature sensor can be a thermometer (for example a pyrometric thermometer which captures the temperature at the measuring surface by detecting its heat radiation) which contactlessly captures a temperature at the measuring surface. It is also possible to form the calibration-temperature sensor by means of a thermometer which is at least temporarily (together with the measuring apparatus-temperature sensor) insertable in a sample carrier which at least partially delimits the measuring surface. Other types of thermometers can also be utilized.

According to an exemplary embodiment, the measuring apparatus-calibration device may comprise a thermal shielding. Depending on the case of application, the thermal shielding can comprise a thermally conductive shielding (in particular a thermally high conductive shielding), in which the calibration-temperature sensor is partially (and preferably an additional reference-temperature sensor described below in more detail) arranged, or may also comprise a thermally insulating shielding (in particular when the calibration-temperature sensor is the only temperature sensor of the measuring apparatus-calibration device). The material of a thermally conductive shielding may comprise a value of thermal conductivity of at least 1 W/mK, in particular at least 10 W/mK, further in particular at least 50 W/mK. By thermally shielding the calibration-temperature sensor, the accuracy of the calibrating can be significantly increased. The thermal shielding may for example be formed as a substantially circular cylindrical body with an inner cavity for accommodating the temperature sensor, optional with an end-region which is tapering towards a measuring tip of the calibration-temperature sensor. If, as described below in more detail, in addition to the calibration-temperature sensor a reference-temperature sensor is provided (see FIG. 3 or FIG. 4), the thermal shielding should be formed thermally conductive. If, in contrast to this, only the calibration-temperature sensor is provided as solely temperature sensor of the measuring apparatus calibration device (see FIG. 2), it is advantageous to form the thermal shielding thermally insulating.

According to an exemplary embodiment, a measuring tip of the calibration-temperature sensor to be thermally coupled to the measuring surface may be out of contact with the thermal shielding and may be exposed externally. Thereby it can be ensured that the temperature measuring by the measuring tip of the calibration-temperature sensor which may have contact to the measuring surface or the sample is not disturbed by an (in particular good heat conductive) thermal shielding. This in turn positively effects the accuracy of the calibration.

According to an exemplary embodiment, a back side of the calibration-temperature sensor which is facing away from the measuring tip may be in contact with the thermal (in particular thermally conductive) shielding. Thereby, undesired heat flows to and from the environment can be prevented or suppressed.

According to an exemplary embodiment, the measuring apparatus-calibration device may comprise a reference-temperature sensor with a measuring tip which is surrounded by the thermal (in particular thermally conductive) shielding substantially fully circumferentially. The reference-temperature sensor thus descriptively can be in good thermal contact with the thermal shielding and capture the temperature of the thermally conductive shielding. The knowledge of this temperature enables to perform the calibration with a further improved accuracy.

According to an exemplary embodiment, the measuring apparatus-calibration device may comprise a shielding-tempering unit (which may be formed as temperature regulation), in particular a heating unit and/or a cooling unit, which is adapted for tempering the thermally conductive shielding for reducing or even eliminating a difference between the temperature values captured by the calibration-temperature sensor and the reference-temperature sensor. For example, the shielding-tempering unit may be formed as thermoelectric element (for example a Peltier element). By applying an electric current to such a thermoelectric element, thermal energy can be selectively supplied to or discharged from the thermally conductive shielding, in order to reduce a difference between the temperature measured by the calibration-temperature sensor and the temperature measured by the reference-temperature sensor. For example, the control or regulation of the shielding-tempering unit may be carried out, such that the difference between the both temperatures decreases below a pre-givable threshold value, in particular disappears. A heating unit and cooling unit has the advantage over a pure heating unit, that deviations between the both measured temperatures with both signs can be compensated.

According to an exemplary embodiment, the calibration-temperature sensor and/or the reference-temperature sensor may be separable from (in particular extractable from) the thermal shielding. By forming preferably both mentioned temperature sensors separable and removable, respectively, from the thermal shielding, both temperature sensors can be subjected to an own re-calibration, respectively separated from each other, if necessary, whereby the accuracy of a calibration probe with an actively temperable thermally conductive shielding becomes remarkably high.

According to an exemplary embodiment, the determination unit may be adapted for determining a correction value by which the measuring apparatus-temperature captured by the measuring apparatus-temperature sensor is to be corrected, in order to adjust (and calibrate, respectively) the measuring apparatus-temperature sensor. The quantity of the correction value corresponds to the difference between the temperatures at the measuring surface, as they are measured by the calibration-temperature sensor and the measuring apparatus-temperature sensor. The quantity of the correction value itself may be different for different, actual temperatures at the measuring surface, can correspondingly be calculated differently and stored differently.

According to an exemplary embodiment, the measuring apparatus may comprise an electromagnetic measuring radiation source (for example a light emitting diode or a laser) for emitting electromagnetic measuring radiation onto the sample applied on the measuring surface and may comprise an electromagnetic measuring radiation detector (for example a detector which is sensitive for a position, for example a one-dimensional or two-dimensional array of sensor elements which are sensitive to radiation) for detecting the electromagnetic measuring radiation after an interaction of the sample with the electromagnetic measuring radiation.

According to an exemplary embodiment, the measuring apparatus may comprise a sample carrier which is penetrable (in particular optically transparent) by electromagnetic measuring radiation for measuring the sample, which defines or delimits the measuring surface for accommodating the sample, and at and/or in which the measuring apparatus-temperature sensor is fixed. If the measuring apparatus is formed as refractometer for determining the value of a refractive index of a sample, the sample carrier may be a reference-solid body which is translucent for the electromagnetic radiation, for example a measuring prism or a measuring hemisphere. On a top side, the sample can be applied onto the measuring surface of the sample carrier, on a bottom side, incident electromagnetic primary radiation can be brought in interaction with the sample through the reference-solid body and, after the interaction with the sample, respective electromagnetic secondary radiation can propagate through the reference-solid body towards an electromagnetic radiation detector.

According to an exemplary embodiment, the measuring apparatus may comprise a sample carrier-tempering unit, in particular a heating unit and/or a cooling unit, which is adapted for tempering the sample carrier, in order to bring the sample carrier to a pre-givable temperature. With such a sample carrier-tempering unit, it is possible to bring (in particular to regulate) the sample carrier and thus the sample to a desired temperature. For example, the sample carrier-tempering unit may be formed as thermoelectric element (for example a Peltier-element) in cooperation with a control unit or regulating unit. By applying an electric current to such a thermoelectric element, thermal energy can be selectively supplied to the sample carrier or discharged from it.

According to an exemplary embodiment, the adjusting unit may be adapted to, based on the information which is determined by the determination unit for different pre-given temperatures of the sample carrier, differently adjust the measuring apparatus-temperature sensor for the different pre-given temperatures. According to this embodiment, by means of the sample carrier-tempering unit, for example (i) a certain temperature of the sample carrier can be set, (ii) the calibration can be carried out using the measuring apparatus-calibration device, and (iii) a respective quantitative calibration value for a temperature correction at this temperature can be stored in a database. In this way, a set of data can be collected which allows a correction for each actual temperature of the sample carrier.

According to an exemplary embodiment, the measuring apparatus may be formed as refractometer which determines an information which is indicative for the refractive index of the sample from a critical angle of a total reflection at a boundary surface between the sample on the measuring surface of a reference-solid body (as sample carrier) and the reference-solid body, in particular a prism or a hemisphere.

According to another exemplary embodiment, the measuring apparatus may be formed as an infrared spectrometer, wherein in such an optical measuring apparatus infrared radiation is used as measuring probe.

In particular, the measuring apparatus may be formed as an ATR-(Attenuated Total Reflection) measuring cell. ATR-infrared spectroscopy is a measuring technique of the infrared spectroscopy for the surface examination of non-transparent samples, wherein the intensity of the reflected light is measured, which allows for conclusions about the absorbing medium, i.e. the sample.

Furthermore, the measuring apparatus may be formed as FTIR-spectrometer (Fourier-transformation-infrared spectrometer). An FTIR-spectrometer is a spectrometer for the infrared spectroscopy, wherein a spectrum is not recorded by a stepwise changing of the wavelength, but instead is calculated by a Fourier-transformation of a measured interferogram.

According to an exemplary embodiment, the measuring apparatus-calibration device may be formed separately from the (in particular optical) measuring device, in particular attachably thereon and/or detachably therefrom, such that, after separating, the measuring apparatus-calibration device is utilizable for calibrating another (in particular optical) measuring apparatus. In this way, one single calibration device can be used resource-savingly for calibrating many different measuring apparatuses. For example, the calibration device can be utilized as portable calibration probe which can be attached onto a measuring apparatus (for example onto a measuring surface thereof) and can report information resulting from the associated measurement back to the measuring apparatus, in order that in an interior of the measuring apparatus, an adaption of the measuring temperature assessment can be performed for the purpose of calibrating.

According to an exemplary embodiment, the measuring apparatus-calibration device and the in particular optical measuring apparatus may be formed such that the measuring apparatus, after separating the measuring apparatus-calibration device from the measuring apparatus, is operable for (in particular optical) measuring a sample. After detaching the calibration device from the measuring apparatus after finishing the calibration, only the sample has to be applied onto the measuring surface and the measuring can start. The effort in conjunction with a re-calibrating of the measuring apparatus is therefore extremely low.

According to an exemplary embodiment, the method may comprise an adjusting of the measuring apparatus based on the information indicative for the discrepancy, such that the measuring apparatus-temperature is corrected. Thereby, the adjusting is completed.

According to an exemplary embodiment, the calibrating and/or adjusting of the measuring apparatus may be performed while the measuring apparatus is located at a user for an operation in the field. By means of a calibration device which is portable and preferably not intervening into the sensor path of the measuring apparatus, the calibrating can also be performed without technical knowledge at the user, without the need that the complex measuring apparatus has to be sent to a manufacturer for calibrating.

According to an exemplary embodiment, when calibrating, the measuring apparatus can be tested upon its temperature measuring properties without intervening in a sensor path of the measuring apparatus, in particular without opening the measuring apparatus. This ensures a high measuring accuracy of the measuring apparatus, since a detuning or misadjusting of a set-up of optical components in the measuring apparatus, which is threatening by an intervention in the sensor path or the interior of the measuring apparatus, is prevented.

BRIEF DESCRIPTION OF THE DRAWINGS

In the following, exemplary embodiments of the present invention are described in detail with reference to the following figures.

Same or similar components in different figures are provided with the same reference numerals.

Before, referring to the figures, exemplary embodiments of the invention are described, some general aspects of the invention and the underlying technology shall be explained:

According to an exemplary embodiment of the invention, an effective and simple calibration of the measuring surface temperature of measuring apparatuses and laboratory apparatuses, respectively, is enabled.

A method according to an exemplary embodiment of the invention provides a measurement, wherein the substance or sample to be measured in the measuring operation is arranged at a measuring surface (for example of a reference-solid body and sample carrier, respectively) of the measuring apparatus and this measuring surface is not located in the interior of the measuring apparatus, but intentionally is accessible from the outside for a user handling the sample. In such a geometry, especially in optical measuring apparatuses, it is difficult to accurately measure the temperature of the measuring surface and thus of the sample, and to calibrate an measuring apparatus-temperature sensor which is in particular implemented below the measuring surface in the measuring apparatus, respectively.

An example for such a measuring apparatus is a refractometer which operates according to the principle of partial total reflection of light at the measuring surface, i.e. the boundary surface between the sample carrier and the reference-solid body (for example a measuring prism), respectively, and the sample. Another example for a measuring apparatus according to an exemplary embodiment of the invention is an infrared spectrometer with ATR-measuring cell (Attenuated Total Reflection), in which the sample is illuminated under total reflection and the absorption of the light which penetrates into the sample by means of the evanescent wave is measured.

Sample properties measured with optical measuring methods depend on surrounding conditions. These are normally at least the temperature of the sample and, depending on the measuring process, further quantities, in refractometers and FTIR-spectrometers for example the wavelength of the light.

According to an exemplary embodiment of the invention, preferably a traceable calibration of the measuring surface-temperature is carried out, wherein a calibration of optical measuring apparatuses can be performed with a measuring surface/sample surface. A finding is based on that, for a reasonable calibration of a target quantity, previously the temperature (and if necessary further auxiliary quantities) should be calibrated separately. For example, in a refractometer it is advantageous to adjust the temperature and the wavelength before the refractive index is calibrated or adjusted with reference samples.

According to a preferred embodiment, a temperature-calibration of a surface of a measuring apparatus (such as a refractometer) is performed. Especially preferred, but not mandatory is in this conjunction the use of an actively thermally shielded surface temperature sensing device as measuring apparatus-calibration device for the temperature calibration of a measuring apparatus-temperature sensor which for example can be arranged under a measuring surface of the measuring apparatus (for example a refractometer, FTIR ATR cells). According to another embodiment of the invention, the calibration is carried out with a PT-100 Chip resistance which is adhered to the measuring surface, for example by means of heat conductive paste. The active shielding is indeed highly advantageously and may lead to higher accuracies, but it is not mandatory.

An idea according to an exemplary embodiment consists in to accomplish a method for calibrating the measuring surface temperature with an arbitrary surface thermometer. Alternatively to a surface thermometer, also insertable reference sensing devices are possible.

In the following, it is described why a separate calibration and adjustment of the measuring surface temperature of a refractometer is advantageous in order to enable an adjustment of the refractive index-measurement which is valid for many samples and surrounding conditions.

Refractometers are calibrated by measuring reference substances with a known refractive index. The suchlike determined discrepancies are then used for adjusting the refractometer, if necessary. Commonly, it is assumed that with some few calibration measurements, a sufficient accuracy can be achieved.

This is highly desirable, since on the one hand certificated reference substances are relatively expensive and on the other hand the time effort for a calibration or adjustment shall be reduced.

In particular, it has been established to perform a calibration measuring, often with high-purity water as reference substance, and to use the result for a so-called one-point adjustment. The expectation is that in this way an error of the sensor technology for a large range of refractive indices and/or temperatures can be compensated.

A more detailed contemplation of the error contributions results in that the refractive index measured by a refractometer is not only determined by the actual refractive index of the sample and the measuring errors of the refractive index-sensor technology, but in addition also by errors of the surrounding parameter temperature and wavelength:

$$\tilde{n}(T,\lambda,S)=n(T_0,\lambda_0)+(dn/dT)\Delta T+(dn/d\lambda)\Delta\lambda+\Delta n(S) \quad (1)$$

wherein $\tilde{n}(\lambda, T, S)$ is the direct measuring value of the refractometer at the current sample Temperature T, the current wavelength $\lambda$ of the refractometer and with the measuring errors $\Delta n(S)$ which are caused by the current state of the sensor technology S. Furthermore, dn/dT is the temperature coefficient of the sample, $dn/d\lambda$ is the wavelength dispersion of the sample, $\Delta T=(T-T_0)$ is the temperature error and $\Delta\lambda=(\lambda-\lambda_0)$ is the wavelength error.

It is searched for the refractive index of the substance $n(T_0, \lambda_0)$ at the standard temperature $T_0$ and for the standardized wavelength $\lambda_0$.

When calibrating with reference substances, the deviation between the known reference value and the measuring value $\Delta n=\tilde{n}(T, \lambda, S)-n(T_0, \lambda_0)$ is determined and, if necessary, used in the following adjusting for correction of the measurement values. The deviation according to equation (1) is:

$$\Delta n=\Delta n(S)+(dn/dT)\Delta T+(dn/d\lambda)\Delta\lambda \quad (2)$$

The result, due to temperature errors and wavelength errors, thus is specific for the measured sample. As the temperature coefficient and the wavelength dispersion of the sample themselves in turn are generally temperature dependent and wavelength dependent, the result is also specific for the temperature and the wavelength during the measuring.

This becomes problematic when in the course of an adjustment this result shall be transferred to other samples and other temperatures or wavelengths.

In order to illustrate this, as an example a refractometer with a sensor technology-error $\Delta n(S)$ is contemplated, which error itself is not dependent on the temperature. Water, as well known, has a temperature coefficient dn/dT which is strongly varying with the temperature. The common adjustment with water as reference substance would therefore according to equation (2) lead to a temperature dependent correction value $\Delta n(T)$. The adjustment would therefore only be valid for the temperature at the moment of the adjustment, although the refractive index-sensor technology of the refractometer itself is temperature independent.

The objective of a calibration or adjustment of the refractive index-measuring which, with as few measurements as possible, preferably for all samples in a temperature range and a wavelength range as wide as possible achieves a desired accuracy, can thus be achieved when the errors of the surrounding parameters temperature and wavelength are reduced.

The temperature coefficients dn/dT of different substances indeed vary, but normally do not exceed a value of some $10^{-4}$ refractive index units per Kelvin.

In order to estimate an order of magnitude for the permissible temperature error, a temperature coefficient of a practical reference sample of $4 \times 10^{-4}$ [1/K] and an error contribution which is acceptable for precision refractometers of $1 \times 10^{-5}$ refractive index units is assumed and a permissible temperature error of $\Delta T=0.03°$ C. is obtained. This is a very hard requirement which according to exemplary embodiments of the invention in contrast to conventional approaches, can be fulfilled and can also be maintained over longer time intervals.

In the following, the calibration and adjustment of ATR-measuring cells in FTIR-spectrometers is described. In a content analysis of multicomponent mixtures, with the aid of infrared spectroscopy, from the multiplicity of superimposed spectra of the single components conclusions are drawn to the composition of the sample. For a quantitative content analysis, chemometrical algorithms are utilized. For applicatively desired accuracies, on the one hand the temperature dependent changes of the spectra are relevant, but on the other hand also the temperature dependent interactions between the ingredients among each other (so-called matrix effects).

In chemometric methods, in a first step, from a multiplicity of reference samples, a mathematical model for the application is formed and installed on the measuring apparatuses. When measuring an unknown sample, from the measured spectrum, the content analysis is then performed with the aid of the chemometric model.

In order to achieve the desired accuracies, the temperature of the samples during the measuring for the modeling must not deviate too strong from the sample temperature during the later measuring in the application. The measurements for the modeling normally take place in other apparatuses than the applicative measurements.

Therefore, it is not sufficient for the highest accuracy requirements to realize a reproducible, long term stable temperature measuring in the respective measuring device. In order to generate an absolute temperature accuracy with which the transferability of the chemometric model from a measuring device to another can be ensured, it is advantageous, that the temperature measuring has to be traceably calibratable to (for example national) standards.

For a demanding quantitative spectroscopic analysis, similar temperature accuracies are required as in the refractometer.

Transmission measuring cells can be utilized which however, due to the narrow slit width, easily clog. Thus, increasingly ATR-measuring cells assert themselves, in which the sample is applied onto the measuring surface or is guided to the measuring surface through a flow-through cell which is easily removable and thus easy to clean.

In the following, errors shall be described which may occur during the temperature measuring of the measuring surface-temperature.

Firstly, errors may be caused by thermal gradients. Both, in refractometers and in an ATR cell, the measuring surface is located at the outer side of the measuring apparatus. A temperature sensing device and a measuring apparatus-temperature sensor, respectively, which is integrated in the measuring apparatus, shall measure the surface temperature of the measuring cell, but cannot be mounted directly beneath the surface, since this should remain freely through-illuminatable by a measuring beam.

By a regulated tempering, the temperature of the temperature sensing device and the measuring apparatus-temperature sensor, respectively, can be brought to the desired set-point temperature. Since the measuring surface is located at the outer side of the measuring apparatus, there is the risk that between (a) the (normally unknown) environmental temperature which is present at the measuring surface and (b) the regulated temperature at the location of the integrated temperature sensing device and the measuring apparatus-temperature sensor, respectively, a heat flow and thus a temperature gradient establishes which directly leads to a temperature error of the surface temperature measuring. Such a systematic temperature error can only be determined by a sufficiently accurate measuring of the surface temperature and can thereupon be at least partially compensated by adjusting.

In the following, errors are described which occur by the temperature sensing device and the measuring apparatus-temperature sensor, respectively, and a measuring transducer which evaluates a respective sensor signal.

A required high accuracy of the temperature measuring (for example 0.03° C., or in other cases better than 0.1° C.) requires high-quality temperature sensing devices and measuring apparatus-temperature sensors, respectively. In order to fulfill high accuracy requirements, platinum-resistance-sensing devices (for example PT100, PT1000, PT50) can be used. Also thermistors may be utilized for such precision measurements. Also thermoelements are possible. In order to achieve a high target accuracy, it is advantageous to individually calibrate the temperature sensing device and measuring apparatus-temperature sensors, respectively.

Conventionally, those sensing devices are calibrated and then are firmly mounted into the measuring apparatus. The sensing devices can be mounted in a bore hole in a component by a heat conductive paste or heat conductive adhesive. However, in this case there is the risk that during mounting the sensing devices do not have a sufficient contact to the component part, since they have not been inserted into the bore hole far enough, not enough heat conductive paste or heat conductive adhesive has been applied, or an enclosed air bubble hinders the contact, for example. There is also the risk that temperature sensing devices are mounted mechanically tensioned or a tension is yielded by a shrinking of the heat conductive paste. It is also possible that a tension-freely mounted temperature sensing device is tensioned only in certain temperature ranges by a different thermal expansion of the involved components. Mechanical tensions then lead to measuring errors. Therefore, it cannot be reliably assumed that a mounted sensing device complies with its previous calibration in the context of the required target accuracy. The sensing device in this case has to be re-adjusted after its mounting.

Temperature sensing devices which can be utilized as measuring apparatus-temperature sensors, in addition are subjected to aging and partially react sensitive to external influences like a mechanical shock or a thermal alternating load. The latter indeed occurs in modern refractometers and other measuring apparatuses, wherein the covered temperature ranges may indeed be 100° C. Also an electronic circuit (measuring transducer) which reads the temperature sensing device and the measuring apparatus-temperature sensor, is subjected to a temporal drift.

Already for temperature sensing devices with an accuracy of 0.1° C., conventionally a re-calibration in annual intervals is required. With a target accuracy of 0.03° C., this is therefore mandatory in order to reliably maintain this accuracy also over time.

In the following, calibration and adjustment are discussed: a calibration may in particular in a first step determine the deviation of (a) an (in particular non-calibrated) measuring value of a standard which is determined by a measuring system or measuring apparatus from (b) a pre-known value of this standard. Further in particular in a second step, from the information determined in the first step, a correction may be formed. In order to obtain a valid (calibrated) measuring value, the correction can then be applied to the non-calibrated measuring value, for example by the user or a subordinated information processing unit, so in particular external of the measuring apparatus. An adjustment of a measuring system or measuring apparatus on the other hand may in particular change the measuring apparatus such that it afterwards displays another (in particular improved) value.

This can for example be achieved by carrying out the above described second step of a calibration not externally by the user, but running in the measuring apparatus itself, the measuring apparatus thereby can be varied, i.e. adjusted.

Within this application, calibration may denote in the more narrow sense in particular the first step of the above described general calibration, adjustment may however denote in particular each change of the measuring apparatus, so in particular also the incorporation of the correction process (corresponding to the second step of the above general calibration) into the measuring apparatus.

The above considerations show that the target quantity can be measured sufficiently accurate only in the case when surrounding conditions are fulfilled sufficiently enough. This means that it is advantageous to perform an adjustment after calibrating a temperature error or wavelength error, that is capturing of deviations. In the case of the temperature this means that the measured temperature is corrected correspondingly to the calibration. Thereby it is achieved that the temperature regulation brings the sample to the correct temperature. In an analog temperature regulating, for adjusting a changeable component part (for example a potentiometer) can be matched. This component part can be adjusted by hand. The adjustment of the component part can also be performed by a control (for example a calculator or processor) in an electronic, in particular digital way (in particular with a digital-analog-converter or a digitally adjustable potentiometer).

According to an exemplary embodiment of the invention, a calibration of a measuring apparatus can be performed using a measuring apparatus-calibration device which employs a surface-temperature sensing device as calibration-temperature sensor. The accuracy achievable with such an active temperature sensing device is extremely high and can even fulfill the requirement of +/−0.03° C.

Surface temperature measurements indeed are often afflicted with large systematic errors which depend on the concrete mounting situation of the temperature sensing devices. Their (re-) calibrating is thus difficult. Indeed it is possible to at least partially dismount and to externally calibrate an integrated temperature sensing device, but in the mounted state, the thermal gradients lead to large errors. Thus it would be advantageous to be able to calibrate a surface-temperature sensing device in the mounted state.

According to an exemplary embodiment of the invention, this is possible with a respectively accurately calibratable reference-surface thermometer. For this purpose, for further increasing the accuracy, advantageously an active thermal shielding can be implemented in a measuring apparatus-calibration device according to an exemplary embodiment of the invention.

The above considerations thus lead to the following conclusions:

For a technically correct calibration or adjustment of the refractive index-measuring in precision-refractometers and other measuring apparatuses, a surprisingly high accuracy of the temperature measuring of the sample is a precondition.

Errors in the temperature measuring in refractometers can neither be recognized nor remedied with a conventional refractive index-calibration. The same applies for the wavelength.

For a quantitative analysis by FTIR measuring cells and ATR measuring cells, similar large accuracies for the temperature measuring are required (for example better than 0.1° C.).

In such measuring methods, the sample is located on a measuring surface at an outer side of the measuring apparatus. The sample temperature thus should be indirectly determined via the surface temperature of the measuring surface. This in turn should be measured with a temperature sensing device which is integrated in the vicinity of the surface.

The required accuracy cannot be achieved by temperature sensing devices which are calibrated prior to mounting, which are firmly mounted in the measuring apparatus.

The required accuracy cannot be durably ensured by temperature sensing devices which are calibrated after mounting, which are firmly mounted in the measuring apparatus.

In the light of the foregoing considerations, according to an exemplary embodiment of the invention, a method for a calibration of a measuring apparatus-temperature sensor of a measuring apparatus (in particular for a refractive index-measuring with a refractometer) is provided, wherein an independent calibration and, if necessary, an adjustment of the temperature measuring of the measuring apparatus-temperature sensor with an external, traceable temperature measuring can take place via the measuring surface of the measuring apparatus by a calibration-temperature sensor.

Optionally, it is further possible to perform a calibration and if necessary an adjustment of the refractive index-measuring by measuring of traceable reference substances. With regard to the example of a refractometer as measuring apparatus, such a refractive index-adjustment is advantageous. In this context, the described temperature adjustment is a precondition for achieving a correct adjustment of the refractive index-measuring. In other words, the measured quantity of the measuring apparatus is a property of the sample, not the temperature itself. In other words, it is not per se the objective of such a refractometer or another measuring apparatus to measure temperatures, rather the temperature measuring in the refractometer or another measuring apparatus is a means to an end of measuring the refractive index of the sample or the measuring of another sample related target quantity.

In the following, different embodiments of a calibration of the measuring surface temperature and the measuring apparatus-temperature sensor which is measuring it, according to an exemplary embodiment of the invention, respectively, are described.

The above determined but purely exemplary requirement to the accuracy of a calibration and if necessary an adjustment of the temperature measuring of the measuring surface with 0.03° C. is very high.

Various embodiments of the inventive temperature calibration are possible which differ in particular in the type of the used temperature sensing device and its connection to the measuring surface and the sample carrier, respectively. As calibration-temperature sensor of the measuring apparatus-calibration device, for example a surface thermometer can be advantageously utilized (which may have physical contact with the measuring surface or alternatively can be formed contactlessly). Further, according to other embodiments of the invention, as calibration-temperature sensor a pyrometric surface-thermometer (which performs a contactless measuring of the temperature by determining the radiated infrared wavelength) or a penetrating-sensing device (which can be inserted reversibly and detachably, respectively, into a sample carrier, for example a measuring prism of a refractometer) are possible.

An advantageous property of a calibration-temperature sensor according to an exemplary embodiment of the invention is the traceability of a calibration or adjustment to (in particular national) standards. A traceable calibration complies with the above described high accuracy requirements. For this purpose, it is advantageous to be able to trace the sensors or standards themselves which are used in a calibration or adjustment to (in particular national) standards. This implies that the used sensing devices preferably are not firmly connected to the measuring apparatus and laboratory apparatus, respectively, but can preferably easily be attached and detached, also in the field.

In optical measuring methods, in which the substance or sample to be measured at a measuring surface which is accessible from external, has contact to the optical sensor and is in operative connection with it, respectively, the sample is tempered via this measuring surface. The temperature measuring thus runs indirectly via the optical coupling element and the sample carrier, respectively. In order to achieve an accurate temperature measuring with small errors due to temperature gradients, it is advantageous to position the temperature sensing device and measuring apparatus-temperature sensor, respectively, as near as possible to the location of interest. This however in the mentioned methods is the location of the radiation passage and should remain free for the optics. Therefore not much space remains for the mounting of a temperature sensing device and measuring apparatus-temperature sensor, respectively. A preferred solution is to introduce a blind hole from the inner side of the measuring apparatus into the optical coupling element (i.e. the sample carrier, for example a reference-solid body like a measuring prism) and to adhere or to fix in another way the temperature sensing device and measuring apparatus-temperature sensor, respectively, in this bore hole.

The mentioned gradients in the direction of the measuring surface can be precisely considered with a direct surface measuring. A measuring with a simple surface temperature sensing device as measuring apparatus-calibration device can achieve a sufficient accuracy by connecting the surface temperature sensing device as good as possible to the measuring surface by heat conductive paste, for example, and preferably at the same time an isolation which is as good as possible in the direction of the environment is ensured. In thermoelements this is possible in compliance with certain accuracy requirements. Very high requirements to the accuracy are fulfillable with the use of PT resistances in a four-wire technology. By their larger design and wiring, the isolation yields a very high accuracy only for relatively small temperature differences. These limitations can be reduced by active (that is containing heat regulating) thermal shielded temperature sensing devices as measuring apparatus-calibration device. In this process, by tempering the side of the surface temperature sensing device, which is facing away from the surface to be measured, to the measured temperature, it is prevented or at least reduced that gradients form in the direction to the environment which would otherwise falsify the measuring.

DETAILED DESCRIPTION OF EXEMPLARY EMBODIMENTS

Figure 1:
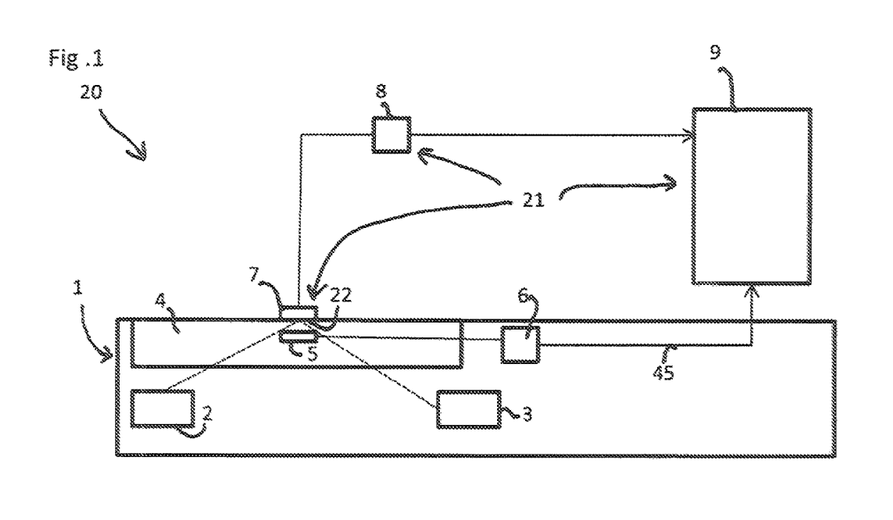
FIG. 1 shows an arrangement of a measuring apparatus and a measuring apparatus-calibration device according to an exemplary embodiment of the invention.

FIG. 1 shows an arrangement 20 of an optical measuring apparatus 1 and a measuring apparatus-calibration device 21 according to an exemplary embodiment of the invention.

The arrangement 20 comprises the optical measuring apparatus 1 which is formed as refractometer for determining a value of a refractive index of a sample which is not shown. The measuring apparatus 1 serves for optical measuring a sample (not shown) which is applicable at a measuring surface 22 of a sample carrier 4 (here in form of a transparent optical element, for example a prims or a hemisphere) by a user.

Firmly or detachably mounted in the measuring apparatus 1 is a measuring apparatus-temperature sensor 5 which is formed as temperature sensing device for capturing a measuring apparatus-temperature in a region of the measuring surface 22. The measuring apparatus-temperature sensor 5 is inserted, in particular adhered, into the optical transparent sample carrier 4, such that an optical sensor path through the measuring apparatus-temperature sensor 5 remains undisturbed.

Furthermore, the measuring apparatus-calibration device 21, which is for example formed as calibration probe, is equipped with a calibration-temperature sensor 7 which is traceably calibratable itself and arranged outside of the measuring apparatus 1, therefore measuring apparatus-external, for determining a calibration-temperature in the region of the measuring surface 22 of the measuring apparatus 1 for calibrating the measuring apparatus-temperature sensor 5. According to FIG. 1, the calibration-temperature sensor 7 which is formed as platinum resistance thermometer, for example, is formed as surface temperature sensor which is attached to the measuring surface 22 in direct physical contact from the outside of the measuring apparatus 1. Heat conductive paste or the like between the calibration-temperature sensor 7 and the measuring surface 22 enhances the thermal coupling and therefore increases the accuracy of the calibrating. Due to providing the calibration-temperature sensor 7 external of the measuring apparatus, the measuring apparatus-calibration device 21 is separatable from the optical measuring apparatus 1 and thus formed as portable calibration probe attachably thereon and/or detachably therefrom. After separating, the measuring apparatus-calibration device 21 can thus be used for calibrating another optical measuring apparatus (not shown). Further, the optical measuring apparatus 1, after separating the measuring apparatus-calibration device 21 from the optical measuring apparatus 1, is operable for optical measuring a sample which beforehand only has to be applied to the measuring surface 22 by a user.

The measuring apparatus-calibration device 21 utilizes the calibration-temperature sensor 7 which is traceably calibratable itself (from a calibration scale not shown in the figure), if necessary, and which is external of the measuring apparatus, for determining a calibration-temperature in the region of the measuring surface 22 of the measuring apparatus 1 and in addition utilizes a determination unit 9 for calibrating. The determination unit 9 (for example a processor) determines a discrepancy and a difference, respectively, between (a) a measuring temperature at the measuring surface 22 which is captured by the measuring apparatus-temperature sensor 5 and (b) the calibration temperature at the measuring surface 22 which is captured by the calibration-temperature sensor 7 (which measured temperatures differ in the case that the measuring apparatus-temperature sensor 5 due to an accuracy loss is misadjusted and is to be re-adjusted). This discrepancy is caused by the fact that the recently adjusted calibration-temperature sensor 7 indeed correctly captures the temperature at the measuring surface 22, but the meanwhile misadjusted measuring apparatus-temperature sensor 5 does not. The discrepancy therefore is straightly a measure for how strong the measuring apparatus-temperature sensor 5 should be re-adjusted in order to error-freely output the actual temperature again. The determination unit 9 is adapted for determining a corresponding correction value with which the measuring apparatus-temperature which is captured by the measuring apparatus-temperature sensor 5 is to be corrected, in order to adjust the measuring apparatus-temperature sensor 5.

As can be taken from FIG. 1, the optical measuring apparatus 1 further comprises an electromagnetic measuring radiation source 2 which is here formed as a light source, for emitting light as electromagnetic measuring radiation onto the sample which is applied on the measuring surface 22. The optical measuring apparatus 1 can use electromagnetic radiation of a suitable wavelength, for example visible light, infrared radiation or ultraviolet radiation. The electromagnetic measuring radiation propagates, as shown in FIG. 1, through the optically transparent sample carrier 4 towards the measuring surface 22 where the electromagnetic measuring radiation is in interaction with the sample which is arranged there during the measuring operation. After this interaction, the electromagnetic measuring radiation can propagate further to an electromagnetic measuring radiation detector 3 for detecting the electromagnetic measuring radiation. The electromagnetic radiation detector 3 may for example be a position-sensitive detector, for example a one-dimensional or a two-dimensional array of photosensitive elements.

Whereas in the calibration operation which is shown in FIG. 1, instead of the sample, the calibration-temperature sensor 7 is attached on the measuring surface 22. The measuring apparatus-temperature sensor 5 is integrated in the sample carrier 4 at a location which is located as near as possible to the measuring surface 22, but does not disturb the propagating of electromagnetic measuring radiation during the measuring operation.

The signal measured by the calibration-temperature sensor 7 is guided to a measuring transducer 8 which can pre-process the signal and can forward it to the determination unit 9. In a corresponding way, the signal measured by the measuring apparatus-temperature sensor 5 can be guided to a measuring transducer 6 which can pre-process the signal and—for example by a (in particular wired or wireless, unidirectional or bidirectional) data transfer connection 45 between the measuring apparatus 1 and the measuring apparatus-calibration device 21—can also forward it to the determination unit 9. The determination unit 9 then can output an output to the user or a connected device (also directly to the measuring apparatus 1) which contains the information how a temperature value which is measured by the measuring apparatus-temperature sensor 5 is to be corrected in order to obtain the true temperature value at the measuring surface 22.

Figure 2:
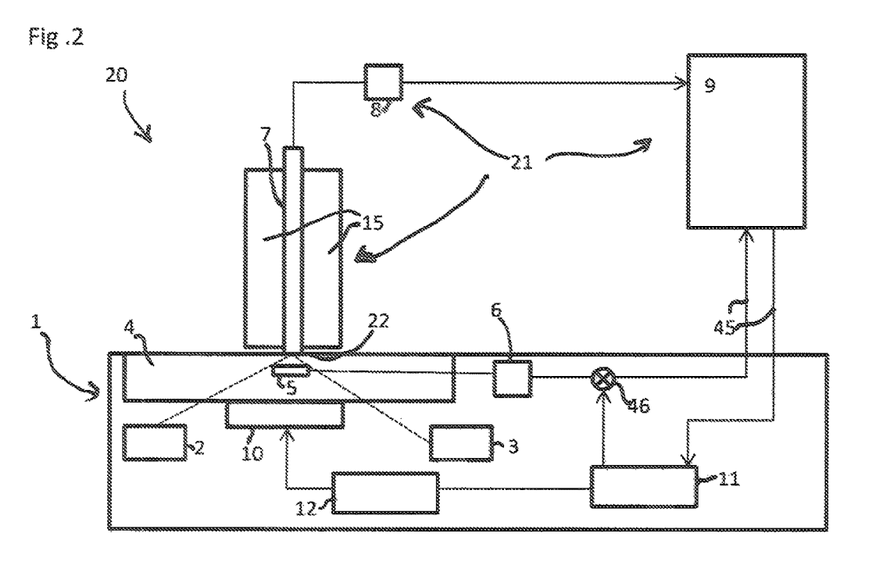
FIG. 2 shows an arrangement of a measuring apparatus and a measuring-calibration device according to another exemplary embodiment of the invention with a temperature regulation of a transparent optical sample carrier.

FIG. 2 shows an arrangement 20 of a measuring apparatus 1 and a measuring apparatus-calibration device 21 according to another exemplary embodiment of the invention.

The measuring apparatus-calibration device 21 according to FIG. 2, in addition to that of FIG. 1, comprises a thermal shielding 15 in which the calibration-temperature sensor 7 is at least partially arranged. A measuring tip of the calibration-temperature sensor 7 projects beyond the shielding 15 and is contacting the measuring surface 22 of the measuring apparatus 1. In other words, the measuring tip of the calibration-temperature sensor 7 to be thermally coupled to the measuring surface 22 is (a) out of contact with the thermal shielding 15 which here is formed thermally insulating, and (b) is externally exposed. The thermal shielding 15 thus thermally decouples the calibration-temperature sensor 7 from the environment and thus increases the accuracy of the calibrating.

In addition to FIG. 1, the optical measuring apparatus 1 according to FIG. 2 further comprises an adjusting unit 11 (which can more general be referred to as control unit or regulating unit and for example may be formed as processor) which is adapted for interacting with the measuring apparatus-calibration device 11 and communicatively coupled, such that by the adjusting unit 11, based on the information which is determined by the determination unit 9 of the measuring apparatus-calibration device 21, the measuring apparatus-temperature sensor 5 is adjustable. For this purpose, the adjusting unit 11 can impinge the temperature which is output at an output of the measuring transducer 6 at a correction unit 46 with an adjusting coefficient which is dependent on the magnitude of the determined discrepancy and compensates it. The determination unit 9 thus transfers to the adjusting unit 11 the result of the comparison between the temperature values which are measured by the measuring apparatus-temperature sensor 5 and the calibration-temperature sensor 7. Depending on the magnitude of the discrepancy, the adjusting unit 11 can impinge the measuring value from the measuring apparatus-temperature sensor 5 with a correction value and a calibration value, respectively, and an adjusting value, respectively.

Furthermore, the measuring apparatus 1 of the arrangement 20 according to FIG. 2 comprises a sample carrier-tempering unit 10 which is formed as a heating unit and/or cooling unit which is adapted for tempering the sample carrier 4 so as to bring the sample carrier 4 to a pre-givable temperature.

According to FIG. 2, in addition a further regulator 12 as a part of the measuring apparatus 1 is provided which now assumes the temperature adjusting of the sample carrier 4 by regulating the sample carrier-tempering unit 10.

Figure 3:
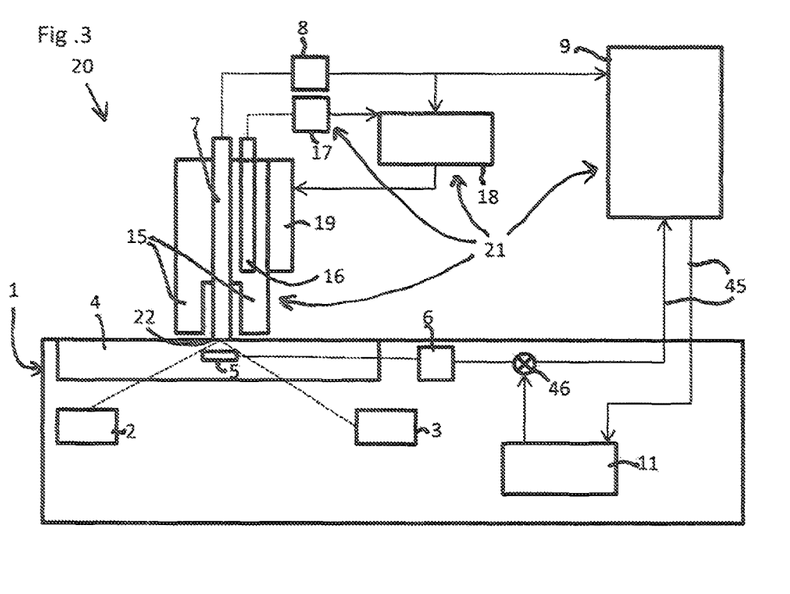
FIG. 3 shows an arrangement of a measuring apparatus and a measuring apparatus-calibration device according to a further exemplary embodiment of the invention.

FIG. 3 shows an arrangement 20 of a measuring apparatus 1 and a measuring apparatus-calibration device 21 according to a further exemplary embodiment of the invention.

According to FIG. 3 (in contrast to FIG. 2), the thermal shielding 15 is made of a thermally highly conductive material. The measuring tip of the calibration-temperature sensor 7 is exposed to the thermal shielding 15. A back side of the calibration-temperature sensor 7 which is facing away from the measuring tip in contrast is in physical and thus thermally conductive contact with the thermally conductive shielding 15. Furthermore, as a part of the measuring apparatus-calibration device 21 according to FIG. 3, an additional reference-temperature sensor 16 with a measuring tip is provided which is surrounded fully circumferentially by the thermally conductive shielding 15, and is therefore in a thermal balance with the thermal shielding 15. The reference temperature sensor 16 measures the temperature of the thermally highly conductive thermal shielding 15 and transmits it to a measuring transducer 17 which pre-processes the measuring data and transmits the measuring data to a regulator 18. Both, the calibration-temperature sensor 7 and the reference-temperature 16 are respectively formed separatable from the thermal shielding, in order to be detachable for an own re-calibration, if necessary. According to FIG. 3, furthermore a shielding-tempering unit 18, 19 is provided in the form of a heating unit and/or cooling unit which is adapted for tempering the thermal shielding 15 for at least partially compensating a difference between the temperature values captured by the calibration-temperature sensor 7 and the reference-temperature sensor 16. The shielding-tempering unit 18, 19 for this purpose comprises the regulator 18 and a heat source/sink 19 (for example a Peltier-element) which is regulated by the regulator 18 on the basis of the supplied actual temperature values.

Figure 4:
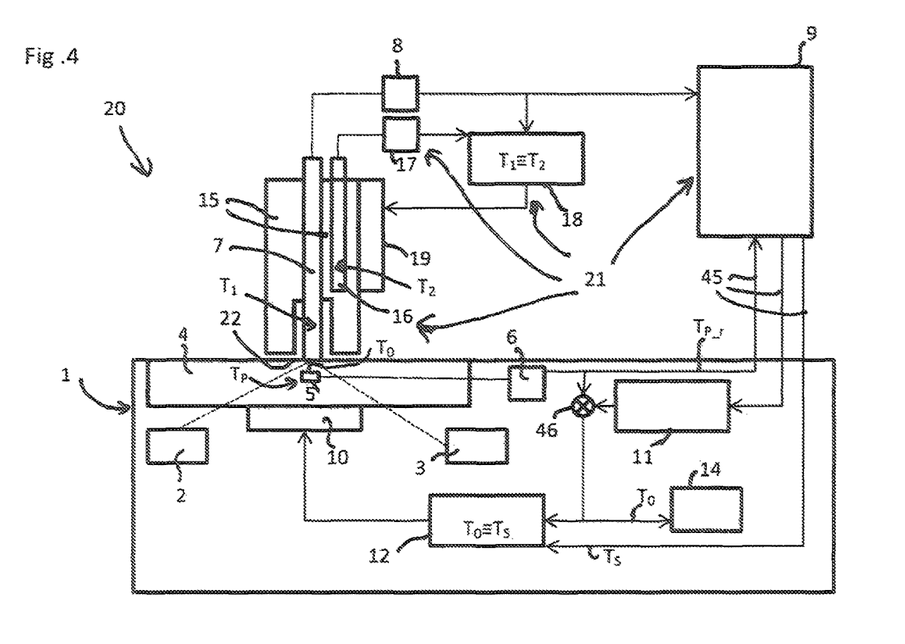
FIG. 4 shows an arrangement of a measuring apparatus and a measuring apparatus-calibration device according to yet another exemplary embodiment of the invention.

FIG. 4 shows an arrangement 20 of a measuring apparatus 1 and a measuring apparatus-calibration device 21 according to yet another embodiment of the invention with a temperature regulating of an optically transparent sample carrier 4. FIG. 4 illustrates the calibration and adjustment of an integrated surface-temperature sensing device (i.e. the measuring-temperature sensor 5) with the active surface thermometer shown in FIG. 7 (formed of the calibration-temperature sensor 7, the reference-temperature sensor 16 and the active thermal shielding 15). In FIG. 4, it is also shown how with an actively shielded surface thermometer in the form of the measuring apparatus-calibration device 21, the temperature sensing device (that is the measuring apparatus-temperature sensor 5), which is integrated in the measuring apparatus 1, can be calibrated and adjusted, if necessary, such that it measures the surface temperature at the measuring surface 22 of the sample carrier 4.

The measuring apparatus 1 contains the integrated temperature sensing device in the form of the measuring apparatus-temperature sensor 5, which is located in the vicinity of the measuring surface 22 of the measuring apparatus 1 which is of interest. This measuring apparatus-temperature sensor 5 with its associated measuring transducer 6 delivers a direct measuring value $T_{P\_r}$. This raw value can be adjusted with the aid of coefficients which are stored in the measuring apparatus 1 (or a not shown externally connected control unit). The adjusted value should correspond to the surface temperature. It may be illustrated on the display unit 14 and/or used internally as auxiliary quantity in the measuring apparatus 1. In the measuring apparatus 1, the surface temperature can be regulated with the aid of a heating unit/cooling unit (cf. sample carrier-tempering unit 10) and a regulator 12 to desired temperatures $T_S$.

As soon as the regulator 18 of the actively shielded surface thermometer has matched the shielding temperature, the calibration-temperature sensor 7 measures the surface temperature with the desired high accuracy.

For example, this temperature can be read and determined, i.e. calibrated, by hand with the value of the calibration-temperature sensor 7 of the measuring apparatus 1. The determined deviation on the one hand is caused by errors of the measuring apparatus-temperature sensor 5 and/or of the measuring transducer 6. However, on the other hand, also systematic deviations of the surface temperature from the temperature in the component part at the location of the integrated measuring apparatus-temperature sensor 5 contribute to the determined deviation.

In a preferred embodiment, the measured surface temperature is fed into a control unit which is also connected to the measuring apparatus 1 and reads the value of the integrated measuring apparatus-temperature sensor 5 which is measured by the measuring apparatus 1. From both values, the control unit calculates the deviation and can in this way calibrate the integrated measuring apparatus-temperature sensor 5.

In measuring apparatuses 1 with a sample carrier-tempering unit 10 (for example a heating device/cooling device) the surface temperature can be actively changed. The integrated temperature sensing device, i.e. the measuring apparatus-temperature sensor 5, in this case can be calibrated at different temperatures. In a preferred embodiment, the temperature which is regulated by the measuring apparatus 1 is pre-given from the connected control unit. The external control unit can then automatedly perform a calibration at multiple pre-given temperatures.

In further exemplary embodiments, the functions of the external control units and, if necessary, the regulator of the surface thermometer and, if necessary, the measuring transducer of the surface thermometer can be integrated in the measuring apparatus 1.

From the deviations determined in the calibration, adjusting coefficients can be determined which can be stored in the measuring apparatus 1. They are used for correction of the direct measuring values $T_{P\_r}$ of the integrated measuring apparatus-temperature sensor 5. In measuring apparatuses 1 without tempering units, the adjusted temperature value can be displayed or used as internal auxiliary quantity. In measuring apparatuses with tempering unit, the adjusted temperature value can be used in the regulator of the tempering unit, such that the regulator can correctly regulate the surface temperature. Both, the errors of the integrated temperature sensing device and that of the associated measuring transducer, like also the systematic deviations of the surface temperature from the temperature which is present in the component part at the integrated sensing device can thereby be compensated.

According to FIG. 4, in addition to FIG. 3, the adjusting unit 11 is adapted for, based on the information which is determined by the determination unit 9 for different pre-given temperatures of the sample carrier 4, differently calibrating the measuring apparatus-temperature sensor 5 for the different pre-given temperatures.

According to FIG. 4, in addition a further regulator 12 as a part of the measuring apparatus 1 is provided which now assumes the temperature adjusting of the sample carrier 4 by regulating the sample carrier-tempering unit 10. The regulator 12 and/or the adjusting unit 11 may transfer data for displaying to a display unit 14 (for example a display).

Alternatively, pyrometric thermometers (not shown) can be utilized for calibration. Pyrometric thermometers have the advantage that they are able to measure the temperature of a surface contactlessly and thus retroactive effect-freely. The materials used for the optical coupling element of the refractometers and FRIT-ATR cells, for example sapphire or diamond, are transparent or partially transparent in the IR wavelength range suitable for the pyrometric measuring and thus are not suitable as a target without further ado. However it is possible to meet this by thermally good conductive attaching a suitable material with high and well-known emissivity (for example a sooted sticky tape) on the measuring surface.

Figure 5:
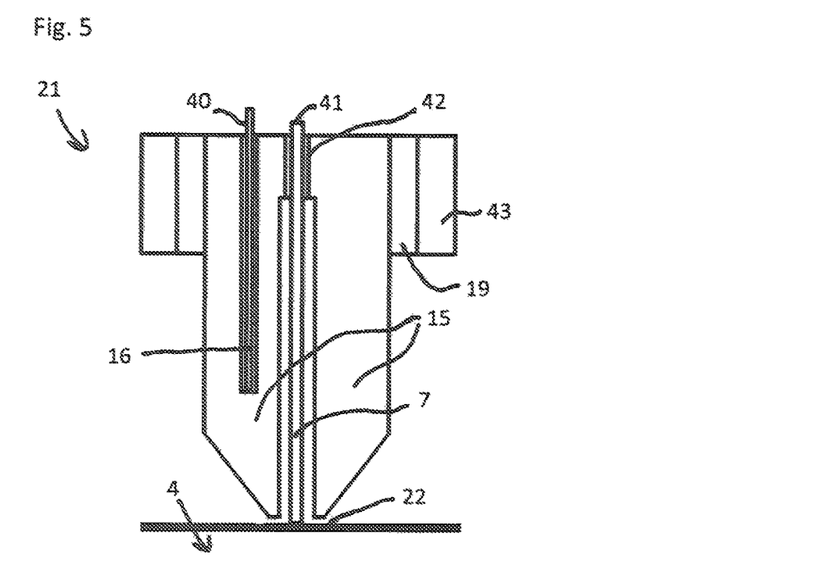
FIG. 5 shows a measuring apparatus-calibration device according to an exemplary embodiment of the invention.

FIG. 5 shows a measuring apparatus-calibration device 21 according to an exemplary embodiment of the invention with an actively shielded surface thermometer.

A heating resistance which is attached in a back region of the calibration-temperature sensor 7 cannot sufficiently shield a relatively large primary resistance sensing device in each case, since the latter has much contact surface with the environmental air.

For example, for precision resistance sensing devices, a temperature shielding made of a thermally good conductive material in the form of the thermal shielding 15 is a preferred solution. The thermal shielding to a large extent surrounds the primary sensing device, i.e. the calibration-temperature sensor 7, such that substantially only that region of the calibration-temperature sensor 7 is not shielded which has contact with the sample and the measuring surface 22, respectively. Thereby, heat flows to the environment through the air are reduced and minimized, respectively.

The thermal shielding 15 in the back part (see reference sign 42) of the calibration-temperature sensor 7 has good thermal contact with the calibration-temperature sensor 7 or its connection cable 40. Thereby, heat flows to the environment through the connection cable 40 are reduced or minimized. In a front part of the calibration-temperature sensor 7 which is facing the sample and the measuring surface 22, respectively, the calibration-temperature sensor 7 is thermally insulated from the thermal shielding 15 as good as possible. Thereby it is prevented that the temperature of the thermal shielding 15 influences the measuring of the surface temperature too strongly. The secondary temperature sensing device, i.e. the reference-temperature sensor 16, is accommodated in the good heat conductive thermal shielding 15 and measures its temperature. Sensor signals can be transmitted from the reference-temperature sensor 16 by the connection cable 41. Here it should be noted that the primary temperature sensing device, i.e. the calibration-temperature sensor 7, touches the surface to be measured, i.e. the measuring surface 22, but not the thermal shielding 15 which is slightly axially backwardly offset with respect to the measuring tip of the calibration-temperature sensor 7.

A special advantage of this configuration is that into the thermal shielding 15, a deep bore hole in the form of a blind hole for the secondary sensing device, i.e. the reference-temperature sensor 16, can be introduced. Thereby it is possible to utilize many types of sensing devices as secondary sensing device, also such which require a relatively large immersion depth, in particular also resistance temperature sensing devices.

Providing only one heating resistance for thermal compensation may be sufficient for surface temperatures above the environmental temperature. For surface temperatures which are both, above and below the environmental temperature, on the other hand, according to an exemplary embodiment of the invention, a heating device and a cooling device can be utilized. Alternatively, according to a further embodiment, it is possible to utilize a merely cooling device for being able to measure surface temperatures below the environmental temperature. Preferably, one or more thermoelectric elements are utilized. According to a preferred embodiment, a temperature which is adjusted by the thermoelectric elements is guided through a component element with a good thermal conductivity (i.e. a temperature conductor) to the primary temperature sensing device, i.e. the calibration-temperature sensor 7.

According to FIG. 5, in particular a cooling body 43 is provided which promotes a heat removal towards the environment. Between the cooling body 43 (which may comprise cooling fins) and the thermal shielding 15, a controllable Peltier-element is provided as heat source/sink 19.

Figure 6:
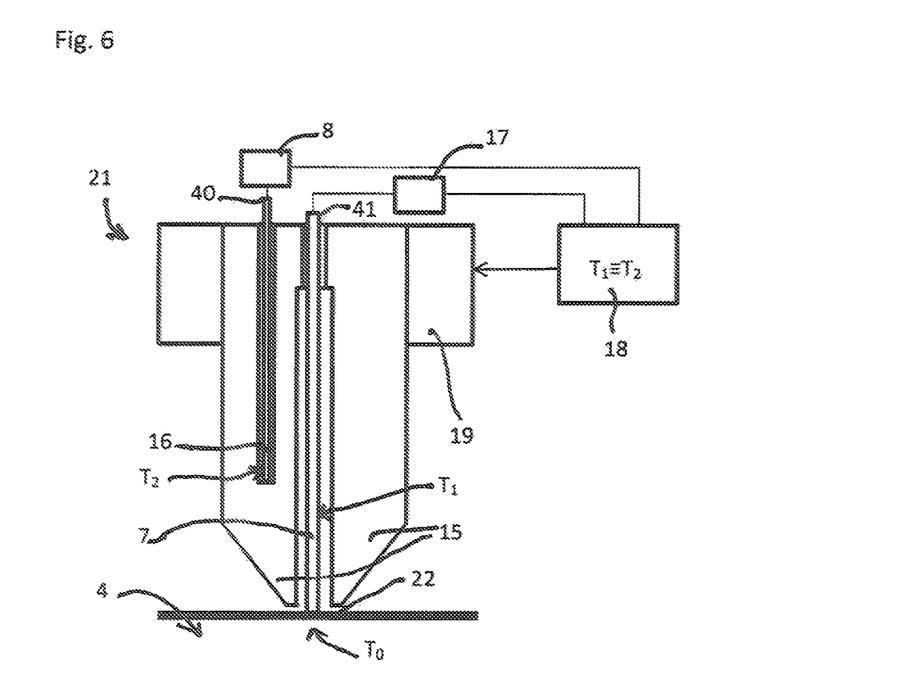
FIG. 6 shows a measuring apparatus-calibration device according to another exemplary embodiment of the invention.

FIG. 6 shows a measuring arrangement with a measuring apparatus-calibration device 21 according to yet another exemplary embodiment of the invention.

In order to measure the surface temperature of the sample carrier 4 in the region of the measuring surface 22, according to FIG. 6:
1. The primary temperature sensing device, i.e. the calibration-temperature sensor 7, is brought into contact with the measuring surface 22, and a temperature $T_1$ is measured,
2. A temperature $T_2$ of the secondary temperature sensing device, i.e. of the reference-temperature sensor 16, is measured and
3. Both temperatures are processed in regulator 18 and a current through the thermoelectric elements as heat source/sink 19 is adjusted which is suitable for reducing the difference.
4. The steps 1) to 3) are repeated until the difference $T_1-T_2$ falls below a pre-givable threshold value. This threshold can be selected such that the remaining influence of the primary temperature sensing device by the slightly differing temperature $T_2$ of the thermal shielding 15 is small enough to achieve the accuracy target.

The temperature $T_1$ then is the measured surface temperature $T_0$.

A special advantage of embodiments of the invention is that there are no special requirements for the size or the design of the temperature sensing devices (see reference sign 7, 16). Standard-immersion sensing devices can be used, for example. A further special advantage of embodiments of the invention is that both temperature sensing devices (see reference sign 7, 16) are detachable from the thermal shielding 15 and can thus be easily traceably re-calibrated externally.

Figure 7:
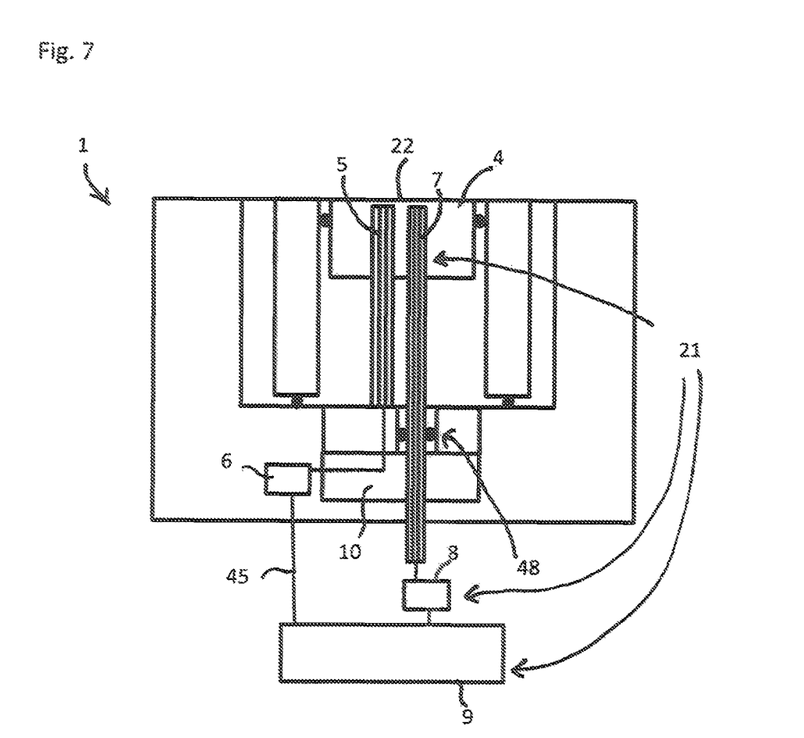
FIG. 7 shows a measuring apparatus with a temporarily integratable measuring apparatus-calibration device according to an exemplary embodiment of the invention.

FIG. 7 shows a measuring apparatus 1 with an integrated measuring apparatus-calibration device 21 according to an exemplary embodiment of the invention. According to FIG. 7, the calibration-temperature sensor 7 is fixed internal of the measuring apparatus in a sample carrier 4 comprising the measuring surface 22. According to such an embodiment, a second bore hole can be introduced at a thermally equivalent location into the coupling element and the sample carrier 4, respectively, in order to insert a reference sensing device (which then operates as calibration-temperature sensor 7) there. Since the sensor technology with the sample carrier 4 is tempered (see reference sign 10) and in general can also be brought below the environmental temperature, it is separated from the environment by an encapsulation, in order to prevent the formation of condensation water from the sensor technology. It is therefore advantageous to provide a temporary and sealable access 48 through the encapsulation to the interior of the measuring device 1, which enables to insert the calibration-temperature sensor 7 from the outside into the bore hole to the measuring position. From the outside normally denotes from the side or lower side of the measuring apparatus 1.

The signal measured by the calibration-temperature sensor 7 is conducted to a measuring transducer 8 which can pre-process the signal and forward it to the determination unit 9. In a corresponding way, the signal which is measured by the measuring apparatus-temperature sensor 5 can be conducted to a measuring transducer 6 which can preprocess the signal and—for example by a (in particular wired or wireless, unidirectional or bidirectional) data transfer connection 45 between the measuring apparatus 1 and the measuring apparatus-calibration device 21—can also forward it to the determination unit 9.

The determination unit 9 then can output an output to a user or a connected apparatus (also directly to the measuring apparatus 1), which contains the information how a temperature value which is measured by the measuring apparatus-temperature sensor 5 is to be corrected, in order to obtain the true temperature value at the measuring surface 22.

Figure 8:
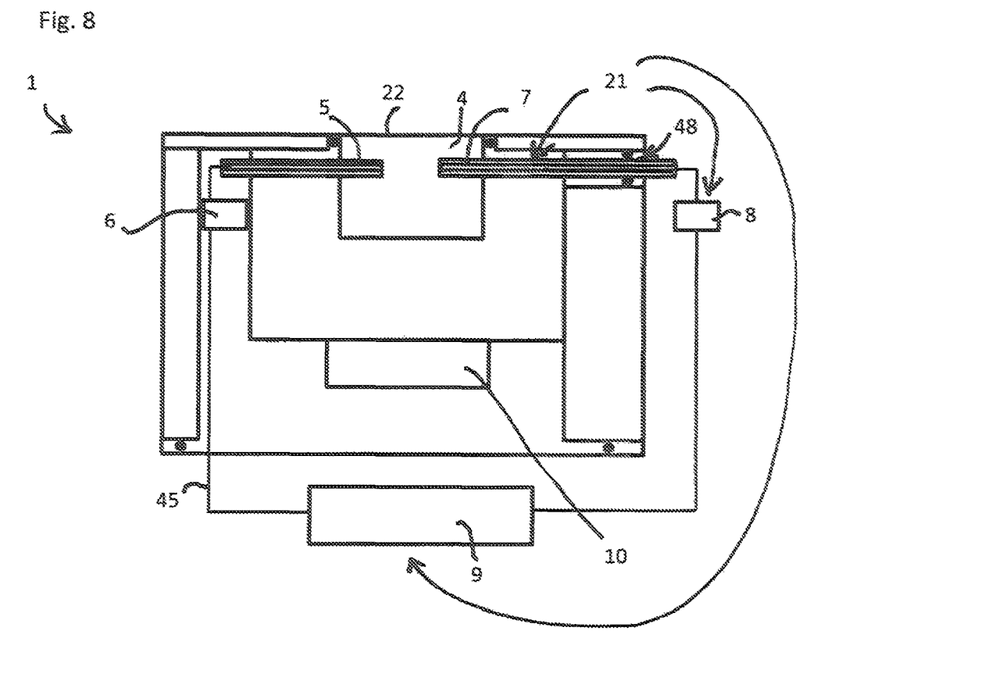
FIG. 8 shows a measuring apparatus with a temporarily integratable measuring apparatus-calibration device according to another exemplary embodiment of the invention.

FIG. 8 shows a measuring apparatus 1 with an integrated measuring apparatus-calibration device 21 according to another exemplary embodiment of the invention, at which the inserting of the calibration-temperature sensor 7 is carried out from a lateral position.

Complementary, it should be noted that "comprising" does not exclude other elements or steps and "a" or "an" does not exclude a multiplicity. Further it should be noted that features or steps which are described with reference to one of the above embodiments can also be used in combination with other features or steps of other embodiments described above. Reference signs in the claims shall not be considered as limitation.

The invention claimed is:

1. A calibration device for calibrating a measuring apparatus-temperature sensor of a measuring apparatus, the calibration device, comprising:
   a calibration-temperature sensor arranged external of the measuring apparatus, which is traceably calibratable for determining a calibration temperature in a region of a measuring surface of the measuring apparatus; and
   a determination unit coupled to the calibration-temperature sensor and a measuring apparatus-temperature sensor arranged in the measuring apparatus, the determination unit adapted for determining an information indicative for a discrepancy between a measured temperature in the region of the measuring surface captured by the measuring apparatus-temperature sensor, and the calibration-temperature, on whose basis the measuring apparatus-temperature sensor is calibratable.

2. The calibration device according to claim 1, wherein the calibration-temperature sensor is a surface temperature sensor for measuring apparatus-external coupling to the measuring surface.

3. The calibration device according to claim 1, wherein the calibration-temperature sensor is selected from a group consisting of a resistance thermometer which is attached to the measuring surface, a pyrometric thermometer unattached to the measuring surface, and a thermometer which is at least temporarily insertable into a sample carrier of the measuring device which at least partially delimits the measuring surface.

4. The calibration device according to claim 1, further comprising a thermal shielding in which the calibration-temperature sensor is at least partially arranged.

5. The calibration device according to claim 4, wherein a measuring tip of the calibration-temperature sensor thermally coupled to the measuring surface is out of contact with the thermal shielding and is exposed externally;
   wherein a back side of the calibration-temperature sensor, which is facing away from the measuring tip, is in thermally conductive contact with the thermal shielding.

6. The calibration device according to claim 4, comprising at least one of the following features:
   the calibration device comprises a reference-temperature sensor with a measuring tip which is surrounded by the thermal shielding substantially fully circumferentially;
   wherein at least one of the calibration-temperature sensor and the reference-temperature sensor is formed separatably from the thermal shielding.

7. The calibration device according to claim 6, further comprising:
   a tempering unit adapted for tempering the thermal shielding for at least partially compensating a difference between the temperature values captured by the calibration-temperature sensor and by the reference-temperature sensor.

8. The calibration device according to claim 1, wherein the determination unit is adapted for determining a correction value by which the temperature captured by the measuring apparatus-temperature sensor is to be corrected, in order to calibrate the measuring apparatus-temperature sensor.

9. An optical measuring apparatus for optically measuring a sample arranged at a measuring surface, wherein the optical measuring apparatus comprises:
   a measuring apparatus-temperature sensor for capturing a temperature in a region of the measuring surface; and
   an adjusting unit communicatively coupled to a determination unit of a calibration device and the measuring apparatus-temperature sensor, the adjusting unit adapted for receiving a control signal from the determination unit and adjusting the temperature as determined by the measuring apparatus-temperature sensor, wherein the determination unit identifies a discrepancy between a temperature identified by a traceably calibratable temperature sensor located external of the measuring apparatus.

10. The optical measuring apparatus according to claim 9, wherein the optical measuring apparatus comprises:
    an electromagnetic measuring radiation source for emitting electromagnetic measuring radiation onto the sample located at the measuring surface;
    an electromagnetic measuring radiation detector for detecting the electromagnetic measuring radiation after an interaction of the sample with the electromagnetic measuring radiation.

11. The optical measuring apparatus according to claim 9, further comprising a sample carrier which is penetratable by electromagnetic measuring radiation for measuring the sample, which defines the measuring surface for accommodating the sample and at and/or in which the measuring apparatus-temperature sensor is fixed.

12. The optical measuring apparatus according to claim 11, comprising a sample carrier-tempering unit adapted for tempering the sample carrier to bring the sample carrier to a desired temperature,
    wherein the adjusting unit is adapted to, based on information which is determined by the determination unit for different desired temperatures of the sample carrier, differently adjust the temperature sensor for the different desired temperatures.

13. The optical measuring apparatus according to claim 9, formed as at least one of the group consisting of a refractometer, an infrared spectrometer, an ATR-measuring cell and an FTIR-spectrometer.

14. An arrangement, comprising:
    an optical measuring apparatus for optically measuring a sample arranged at a measuring surface, the optical measuring apparatus including a measuring apparatus-temperature sensor for capturing a measured temperature in a region of the measuring surface; and a calibration device, with a calibration-temperature sensor, which is traceably calibratable itself, for determining a calibration-temperature in the region of the measuring surface of the measuring apparatus for adjusting the measuring apparatus-temperature sensor.

15. The arrangement according to claim 14, comprising at least one of the following features:

wherein the calibration device is separatable from the optical measuring device with a portable calibration probe attachably thereon and/or detachably therefrom, such that, after separating, the calibration device is usable for calibrating another measuring apparatus;

wherein the calibration device and the optical measuring apparatus are formed such that the optical measuring apparatus, after separating the calibration device from the optical measuring apparatus, is operable for measuring a sample.

16. A method for calibrating a measuring apparatus-temperature sensor of an optical measuring apparatus, wherein the method comprises:

determining a calibration-temperature in a region of a measuring surface of the optical measuring apparatus by a calibration-temperature sensor external of the optical measuring apparatus, which is traceably calibratable itself;

determining an information which is indicative for a discrepancy between a temperature in the region of the measuring surface, which temperature has been captured by a measuring apparatus-temperature sensor; and a calibration-temperature, on whose basis the measuring apparatus-temperature sensor is calibratable.

17. The method according to claim 16, further comprising:

adjusting the measuring apparatus based on the information indicative for the discrepancy, such that the temperature is corrected.

18. The method according to claim 16, further comprising:

calibrating and/or adjusting of the optical measuring apparatus in the field;

wherein, when calibrating, the optical measuring apparatus is tested upon its temperature measuring properties without intervening in a sensor path of the optical measuring apparatus or without opening the measuring apparatus.

19. A method comprising:

measuring, with an optical measuring apparatus, a target quantity which is different from an indication of a temperature from a measuring-apparatus temperature sensor; and calibrating the measuring-apparatus temperature sensor which is mounted in the optical measuring apparatus without intervening in a sensor path of the optical measuring apparatus, wherein calibrating includes:

measuring a surface temperature of the measuring apparatus with a calibration-temperature sensor arranged external of the optical measuring apparatus, the calibration-temperature being traceably calibratable; and determining a discrepancy between a temperature captured by the measuring—apparatus temperature sensor and the surface temperature measured by the traceably calibratable calibration-temperature sensor, on whose basis the measuring-apparatus temperature sensor is calibratable.

* * * * *